US011832827B2

(12) United States Patent
Brom et al.

(10) Patent No.: US 11,832,827 B2
(45) Date of Patent: Dec. 5, 2023

(54) KISSING BALLOONS

(71) Applicant: CAR HOLDING B.V., Maastricht (NL)

(72) Inventors: Henri Lorenzo Frederik Brom, Maastricht (NL); Tjeerd Homsma, Maastricht (NL)

(73) Assignee: CAR HOLDING B.V., Maastricht (NL)

( * ) Notice: Subject to any disclaimer, the term of this patent is extended or adjusted under 35 U.S.C. 154(b) by 349 days.

(21) Appl. No.: 17/275,347

(22) PCT Filed: Sep. 9, 2019

(86) PCT No.: PCT/EP2019/073986
§ 371 (c)(1),
(2) Date: Mar. 11, 2021

(87) PCT Pub. No.: WO2020/053144
PCT Pub. Date: Mar. 19, 2020

(65) Prior Publication Data
US 2022/0096092 A1 Mar. 31, 2022

(30) Foreign Application Priority Data
Sep. 11, 2018 (NL) .................................... 2021601

(51) Int. Cl.
*A61B 17/12* (2006.01)
*A61M 25/10* (2013.01)
*A61B 17/00* (2006.01)

(52) U.S. Cl.
CPC .. *A61B 17/12113* (2013.01); *A61B 17/12186* (2013.01); *A61M 25/1002* (2013.01);
(Continued)

(58) Field of Classification Search
CPC ......... A61B 17/12113; A61M 25/1011; A61M 25/1002; A61M 2025/1015;
(Continued)

(56) References Cited

U.S. PATENT DOCUMENTS

| 6,306,177 | B1 | 10/2001 | Felt et al. |
| 7,670,622 | B2 | 3/2010 | de Vries |
| 2015/0230951 | A1* | 8/2015 | Al-Saadon ............ A61M 25/09 600/585 |

FOREIGN PATENT DOCUMENTS

| EP | 0667131 A2 | 8/1995 |
| EP | 1435249 A1 | 7/2004 |

(Continued)

*Primary Examiner* — Katherine M Rodjom
*Assistant Examiner* — Lindsey R. Rivers
(74) *Attorney, Agent, or Firm* — Hudak, Shunk & Farine Co. LPA

(57) ABSTRACT

An arrangement for implementing kissing balloons simulating a bifurcated vessel, including a first catheter having a first inflatable balloon, a second catheter having a second inflatable balloon, wherein the first balloon includes a holding element that is adapted to receive and hold a distal end of the second balloon and upon inflation of the first balloon and the second balloon to allow formation of a kissing surface between respective facing surfaces of the first balloon and the second balloon inside the holding element, wherein the holding element is designed and connected to the first balloon to prevent the distal end of the second balloon from passing through the holding element. A kit including the arrangement for implementing kissing balloons and a method of manufacturing the arrangement.

22 Claims, 4 Drawing Sheets

(52) U.S. Cl.
CPC .... *A61M 25/1011* (2013.01); *A61M 25/1034* (2013.01); *A61B 2017/00526* (2013.01); *A61B 2017/1205* (2013.01); *A61M 2025/1015* (2013.01); *A61M 2025/1045* (2013.01); *A61M 2025/1052* (2013.01); *A61M 2025/1079* (2013.01)

(58) Field of Classification Search
CPC .. A61M 2025/1045; A61M 2025/1052; A61M 2025/1079; A61M 2025/1081
See application file for complete search history.

(56) References Cited

FOREIGN PATENT DOCUMENTS

| | | | | |
|---|---|---|---|---|
| WO | WO-9416761 A1 * | 8/1994 | ........ | A61M 25/1011 |
| WO | 9508289 A2 | 3/1995 | | |
| WO | 9634580 A1 | 11/1996 | | |
| WO | WO-2011119882 A1 * | 9/2011 | ............. | A61F 2/856 |
| WO | WO-2012037162 A1 * | 3/2012 | ........ | A61M 25/1002 |
| WO | 2013085388 A2 | 6/2013 | | |
| WO | WO-2013085388 A2 * | 6/2013 | ............. | A61F 2/954 |
| WO | WO-2017017259 A1 * | 2/2017 | ............... | A61F 2/04 |
| WO | 2017086791 A1 | 5/2017 | | |
| WO | 2017086793 A1 | 5/2017 | | |

* cited by examiner

KISSING BALLOONS

FIELD OF THE INVENTION

The invention relates to an arrangement for implementing kissing balloons simulating a bifurcated vessel.

The invention further relates to a kit comprising the arrangement for implementing kissing balloons simulating a bifurcated vessel.

The invention still further relates to a method of manufacturing an arrangement for implementing kissing balloons for simulating a bifurcated vessel.

BACKGROUND OF THE INVENTION

Aneurysms in blood vessels in humans or animals can be life threatening. It has therefore been known to bridge such aneurysm using a stent, such that the wall of the aneurysm is isolated from the blood flow through the stent and thus pressure on said wall of the aneurysm is at least reduced and preferably eliminated. To this end a stent is used comprising a closed wall, preventing passage of blood through the wall. For aneurysms at bifurcations special bifurcated stents have been proposed, again having such closed wall. For positioning such bifurcated stents normally multiple guide wires and balloons are used, such that in each leg of a bifurcating blood vessel an end of the stent can be expanded by inflating the relevant balloon, such that the relevant leg closes off against the inside of the relevant leg of the blood vessel. After positioning of the bifurcated stent, the balloons and guide wires are retracted, releasing from the stent that is left behind and afterwards allowing blood flow through the stent. The stent will have to be secured in position in order to maintain proper closure against the blood vessel wall.

More recently as an alternative to the use of stents in bifurcated aneurysms, kissing balloons have been proposed, which are introduced into the relevant bifurcation in a blood vessel, such that they meet inside the aneurysm to be bridged. The kissing balloons form a representation of a channel to be formed bridging the aneurysm. The aneurysmal sac surrounding the kissing balloons in the aneurysm, i.e. the volume surrounding the kissing balloons between the outer surfaces of the balloons and the wall of the aneurysm is then filled using a polymer composition which is allowed to set, forming a filler of the aneurysmal sac. Then the kissing balloons are retracted from the blood vessels and specially the aneurysm, opening the desired channel through the aneurysm, formed by the set polymer.

Such system is known from WO013/085388, which discloses an arrangement for implementing kissing balloons which can be introduced into the aneurysm over a set of guide wires in a known manner. A first one of the kissing balloons is provided with a skirt, which skirt allows passing of a second balloon of the kissing balloons that is guided over a guide wire while the second balloon is still deflated. A portion of the second balloon, located between a distal end and a proximal end of the second balloon, will be pressed against a middle section of the first balloon, located between a proximal end and a distal end of the first balloon, to form a kissing surface upon inflation of the first balloon and the second balloon. Thereafter, the polymer composition is introduced into the aneurysmal sac surrounding the balloons, including the skirt, to completely fill the volume surrounding the kissing balloons between the outer surfaces of the balloons and the inner wall of the aneurysm. After allowing the polymer composition to set, the first and second balloons are deflated and retracted, including the skirt that is attached to the first balloon. In this way, the volume surrounding the kissing balloons between the outer surfaces of the balloons and the wall of the aneurysm is provided with a polymer mold that is left behind in the aneurysmal sac. The polymer mold is provided with a desired bifurcated channel for blood flow extending through or bridging the aneurysm.

Using the arrangement for implementing kissing balloons as discussed in WO013/085388 has the advantage that stents are no longer necessary, preventing the possibility of leaking of blood into an aneurysmal sac surrounding such sac, between a leg of the stent and the vessel wall. It has however been found that this known process may lead to an undesired flow pattern inside the desired bifurcated channel formed and the relevant blood vessel in general.

SUMMARY OF THE INVENTION

It is an object of the invention to provide an arrangement comprising a balloon assembly suitable for simulating a bifurcated vessel, wherein the balloons providing a kissing surface and simulating a main lumen of the desired bifurcated channel formed may be provided in a reliable and reproducible way.

In an aspect of the disclosure an arrangement for implementing kissing balloons simulating a bifurcated vessel is provided, the arrangement comprising a first catheter having a first inflatable balloon and a second catheter having a second inflatable balloon. The first balloon comprises a holding element. The holding element is adapted to receive and hold a distal end of the second balloon and upon inflation of the first balloon and the second balloon to allow formation of a kissing surface between respective facing surfaces of the first balloon and the second balloon inside the holding element. The holding element is designed and connected to the first balloon to prevent the distal end of the second balloon from passing through the holding element.

The person skilled in the art will appreciate that the combination of the holding element and the respective parts of the first balloon and the second balloon that upon inflation of the first balloon and the second balloon form the kissing surface inside the holding element enables a representation of a main lumen of the simulated bifurcated vessel, wherein the representation of the main lumen has an outer surface that runs as smoothly as possible. The thus simulated bifurcated vessel that comprises the representation of the main lumen having the outer surface that runs as smoothly as possible is used to cooperate with a suitable filler, such as a polymer, for filling the aneurysm thereby preventing its disruption. When the filler is form-stable the balloons may be deflated and the catheters with the balloons and the holding element are withdrawn. In this way, the aneurysmal sac is provided with a mold comprising form-stable filler. The form-stable filler of the mold is provided with a passage that corresponds to the simulated bifurcated vessel obtained by the arrangement according to the present invention. The resulting passage within the filler provides a passage for blood. The main lumen of the resulting passage that corresponds to the representation of the main lumen of the simulated bifurcated vessel is confined by a surface of the form-stable filler that consequently runs as smoothly as possible. Because of the smooth surface of the form-stable filler, a blood stream that flows through the main lumen of the mold, when the mold is in use, can have a predominantly laminar flow pattern through the main lumen of the mold that bridges the aneurysmal sac in for example the aorta. The person skilled in the art will appreciate that due to the laminar flow pattern in the main lumen of the mold highly turbulent or stagnant flow areas in the simulated bifurcated vessel can at least be reduced to areas near the bifurcation. Hence, the formation of thrombosis can at least be reduced.

Based on the above, the person skilled in the art will appreciate that establishing the representation of the main lumen of the simulated bifurcated vessel basically depends on compressing two balloons, i.e. the first balloon and the second balloon, inside the holding element to form one composite balloon portion that is enclosed by the holding element. Establishing the representation of the main lumen of the simulated bifurcated vessel starts by inserting the first balloon and the second balloon into a communal artery, for example the aorta, via separate arteries, for example the left femoral artery and the right femoral artery, respectively. The first balloon is provided with the holding element that preferably is arranged midway in an aneurysmal sac of the communal artery, e.g. the aorta. The distal end part of the first balloon is arranged in a healthy part of the aorta past the aneurysmal sac to temporarily block the aorta after inflation of the first balloon. The proximal end part of the first balloon is arranged to block, after inflation of the first balloon, one of the first Iliac artery and the second Iliac artery in a healthy part thereof. The distal end part of the second balloon is accommodated inside the holding element. As mentioned above, the holding element is adapted to prevent the distal end of the second balloon to pass through it. The proximal end part of the second balloon is arranged to block, after inflation of the second balloon, the other one of the first Iliac artery and the second Iliac artery that is not blocked by the proximal end part of the first balloon. The combination of the holding element and the respective parts of the first balloon and the second balloon that upon inflation of the first balloon and the second balloon form the kissing surface inside the holding element enables the combination of the first balloon and the second balloon to form one composite balloon part that provides the representation of the main lumen of the simulated bifurcated vessel. As mentioned above, the representation of the main lumen has an outer surface that runs as smoothly as possible. Consequently, the surface of the form-stable filler that confines the corresponding main lumen of the mold also runs as smoothly as possible.

The balloons may be half or full "dog-bone" balloons. In an advantageous embodiment of the arrangement of the invention, the first balloon is a full dog-bone (FDB) balloon and the second balloon is a half dog-bone (HDB) balloon. However, substantially straight balloons may be used as well.

It will be appreciated that a dimension of a holding element is a compromise between a very small dimension for allowing the first catheter and the second catheter to come into full contact and a relatively large dimension for effectuating an easy introduction of the second catheter into the holding element. It will be appreciated that for differently shaped balloons different rationale may apply for selecting a suitable length of the holding element. For example, for the so-called "dog-bone" balloons the longitudinal dimension of the holding element may be about 30% of the total length of the "dog-bone" balloon. Preferably, in this case, the holding element is provided on the middle portion of the balloon. For the straight balloons a preferable longitudinal dimension of the holding element is about 25% of the total length of the straight balloon. For the straight balloon, the holding element may be provided at a median portion of the balloon.

In a still further embodiment of the arrangement according to the invention the holding element comprises a radiopaque marker. Because the procedure of a catheter introduction is carried out under X-ray real-time imaging the catheter tips are generally provided with a radiopaque marker for visualization purposes. Accordingly, for simplifying location of the holding element on the first catheter the holding element may be advantageously provided with a radiopaque marker. It is possible that the radiopaque marker is dimensioned and configured for indicating the distal and the proximal part of the holding element.

In yet a further embodiment of the arrangement according to the invention, the distal portion of the first balloon has a first cross section, the proximal portion of the first balloon has a second cross section, and the distal end of the second balloon has a third cross section, the first cross section being larger than or equal to a sum of the second cross section and the third cross section. The person skilled in the art will appreciate that in this way the flow rate of the blood stream flowing, for example, from the aorta into the iliac vessels can be kept as constant as possible. In addition, disturbances such as, for example turbulences, in the blood stream flowing, for example, from the aorta into the iliac vessels can be reduced in this way.

In an aspect the disclosure is directed to a kit of parts, comprising an arrangement according to the disclosure and a settable composition, preferably a polymeric composition, wherein the kit of parts preferably further comprises a catheter for introducing the settable composition into a void, such as an aneurysmal sac.

In an aspect the disclosure is further directed to a method of manufacturing an arrangement for implementing kissing balloons for simulating a bifurcated vessel. The method comprises the steps of providing a first catheter having a first inflatable balloon with a holding element arranged on said first balloon, and providing a second catheter having a second inflatable balloon, wherein said holding element is adapted to receive and hold a distal end of the second inflatable balloon upon inserting the distal end of the second balloon in the holding element, wherein upon inflating the first balloon and the second balloon, in use of the arrangement, a kissing surface is formed between respective facing surfaces of the first balloon and the second balloon inside the holding element, wherein the holding element is designed and connected to the first balloon to prevent the distal end of the second balloon from passing through the holding element.

In an aspect the disclosure is directed to a method for forming a mold for a bifurcated channel, wherein a first inflatable balloon is provided having a holding element forming a pocket to a side of the first balloon, and providing a second inflatable balloon having a distal end, wherein the distal end is inserted into the pocket, where after the first balloon and the second balloon are inflated, such that the distal end of the second balloon is enclosed within the pocket and is forced against an outer surface portion of the first balloon inside the pocket, substantially filling the pocket, wherein preferably the outer surface of the holding element and a distal portion of the first balloon directly connecting to the holding element is substantially continuous, wherein proximal portions of the first and second balloons extend from the holding element as substantially separate channel forming mold parts.

The disclosure in an aspect is directed to a method for providing a kissing balloon assembly bridging an aneurysm in a bifurcated vessel, wherein a first inflatable balloon is provided having a holding element forming a pocket to a side of the first balloon, and providing a second inflatable balloon having a distal end, wherein the first balloon is provided bridging an aneurysm in a bifurcating vessel, wherein the distal end of the second balloon is inserted into the pocket inside the aneurysm, where after the first balloon and the second balloon are inflated, such that the distal end of the second balloon is enclosed within the pocket and is forced against an outer surface portion of the first balloon inside the pocket, substantially filling the pocket, wherein preferably the outer surface of the holding element and a distal portion of the first balloon directly connecting to the holding element is substantially continuous, wherein proximal portions of the first and second balloons extend from the holding element as substantially separate channel forming mold parts into vessels leading into the aneurysm.

It is found that introduction of the substantially deformable balloons into a bifurcation is substantially simplified and improved when the balloons may be depleted during introduction and retrieval.

These and other aspects of the invention will be further discussed with reference to drawings which are provided for illustrative purposes only and may not be used for limiting the scope of the appended claims. In the Figures like reference numerals refer to the like elements.

DETAILED DESCRIPTION OF THE DRAWINGS

Figure 2:
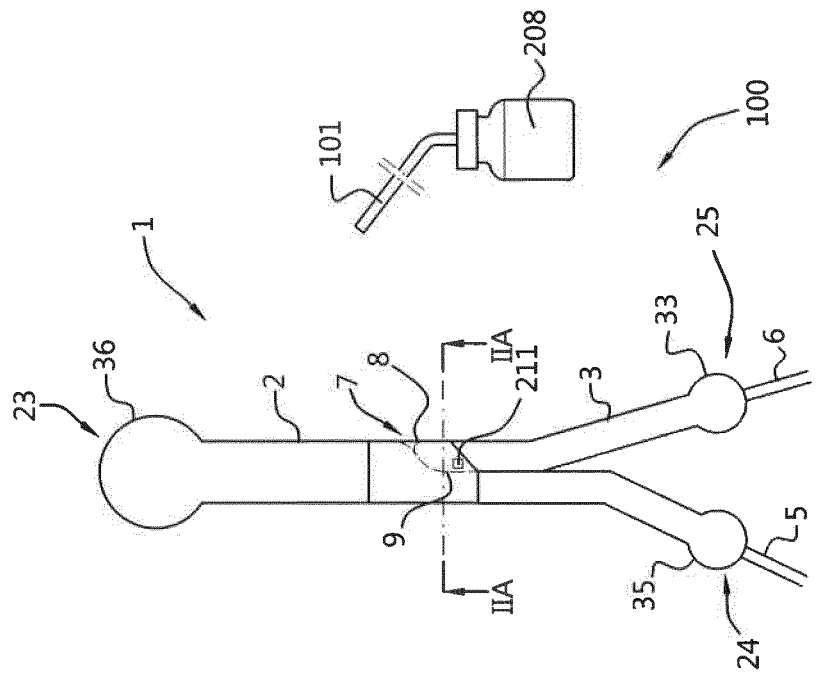
FIG. 2 shows a schematic view of a first balloon with a holding element and second balloon of an arrangement of FIG. 1.

The present disclosure is primarily directed to an arrangement for providing a mold inside in and bridging an aneurysm, using kissing balloons, such that an aneurysmal sac portion formed between the mold and a wall of the aneurysm can be filled with a substance forming a substantially form stable filling, such that after removal of the mold the substance will form a channel bridging the aneurysm, especially a bifurcated channel, which channel preferably has a substantially continuous wall, without dead spaces.

In this disclosure substantially should be understood in its general meaning, that a given value does not have to be met entirely, but relatively small deviations from such value can occur. Substantially can be understood as meaning that for example less than 25% deviation from such value, preferably less than 15%, more preferably less than 10%, such as for example less than 5% is allowable. Such allowable deviations can for example result from production tolerances or material tolerances.

In this disclosure a blood vessel can be any vessel in a human or animal body, such as but not limited to veins and arteries, in any part of the human or animal body. In the description hereafter reference is merely made to patients as being human by way of example. This can however also be an animal.

In this application a distal end or portion of for example a balloon, a catheter, a holding element such as a skirt of the like should be understood as an end or portion of the relevant part or element facing forward upon introduction into a blood vessel. Proximal means the end or portion at an opposite side, trailing when inserted into a blood vessel.

The drawings in general disclose an arrangement 1 for implementing kissing balloons 2, 3 simulating a bifurcated vessel 4, comprising a first catheter 5 having a first inflatable balloon 2 and a second catheter 6 having a second inflatable balloon 3. The first balloon 2 comprises a holding element 7. The said holding element 7 is adapted for receiving a distal end 8 of the second balloon 3, such that upon inflation of the first balloon 2 and second balloon 3 a kissing surface 9 will be formed between facing surfaces 10, 11 of the first balloon 2 and second balloon 3 inside the holding element 7.

Figure 1:
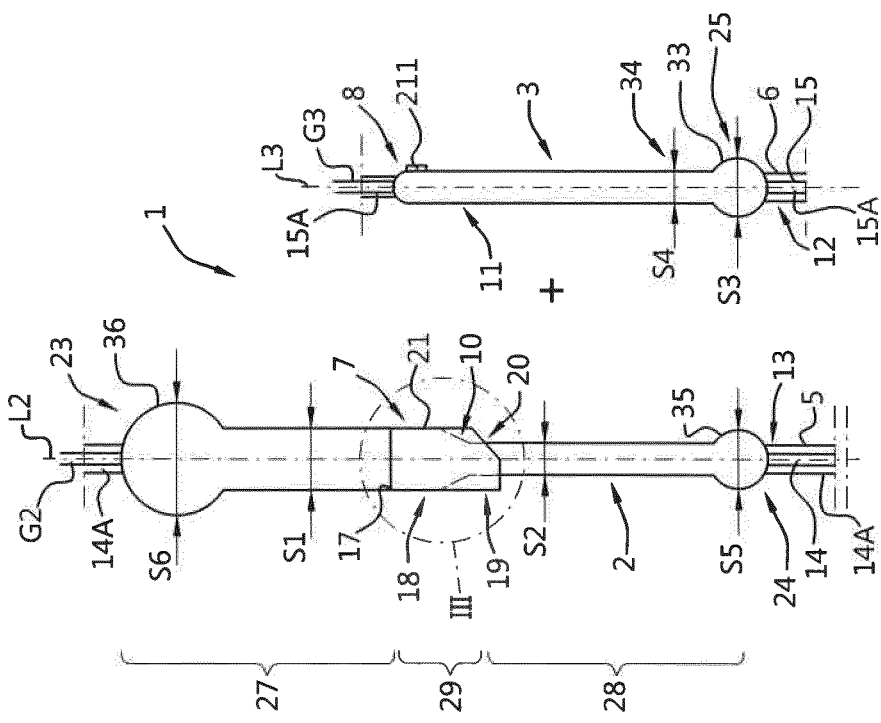
FIG. 1 shows a schematic view of an embodiment of an arrangement for effectuating kissing balloons according to an aspect of the invention, in coupled and inflated position.

FIG. 1 shows an embodiment of the first balloon 2 with part of the first catheter 5 it is connected to, and the second balloon 3 with part of the second catheter 6 to which it is connected, at a distal end 12 of the second catheter 6. The first balloon 2 may be connected to a distal end 13 of the first catheter 5. The first balloon 2 has a longitudinal axis $L_2$, extending between a distal end 23 and a proximal end 24 of the first balloon 2, the first catheter 5 connected to or integral with the proximal end 24 by the distal end 13 of the first catheter 5. The second balloon 3 has a longitudinal axis $L_3$ extending between the distal end 8 and a proximal end 25 thereof, the proximal end 25 being connected to or integral with the distal end 12 of the second catheter 6. The first and second catheter 5, 6 may both be provided with at least one lumen 14, 15, in known manner, for inflating and deflating the respective first and second balloon 2, 3. In embodiments the first and/or second catheter 5, 6 can be provided with a second lumen 14A, 15A, which may extend through or passed the relevant balloon 2, 3, for housing the relevant guide wire $G_2$, $G_3$. In the drawings the balloons 2, 3 are shown in inflated state, unless specified differently.

In advantageous embodiments at least a distal portion of the second guide wire $G_3$ and/or second catheter 5 may be received inside the holding element 7, or between a distal portion 17 of the holding element 7, 16 and the first balloon 2, such that upon at least partial inflation of the first balloon 2 the said distal portion will be caught and fixed in position, further enabling a correct position of the distal end 8 of the second balloon 3 relative to the first balloon 2 and the holding element 7, 16.

In embodiments shown the holding element 7 is designed and connected to the first balloon 2 such that the distal end 8 of the second balloon 3 is prevented from passing through the holding element 7. The distal end 8 of the second balloon 8 can preferably be inserted into the holding element 7 but at least substantially not passed through it, preferably not at all.

In embodiments the holding element 7 can be or comprise a skirt 16 extending around at least part of the outer surface 10 of the first balloon 2. The skirt 16 has a distal end 17 connected to the balloon 2, especially the outer surface 10 thereof, or is integral therewith. Preferably the skirt 16 extends fully around the periphery of a central portion 18 of the first balloon 2, wherein at least part of a proximal end 19 of the skirt 16 is not attached to the surface 10 of the balloon 2, such that at least one pocket 20 is formed between the skirt 16 and the surface 10 of the balloon 2 covered by the skirt 16. A distal side 21 of the pocket 20 is closed by close contact of the distal end 17 of the skirt 16 and the surface 10. For example, by being attached to it or integral with it. The skirt 16 can be connected to the first balloon 2, sealing the skirt 16 against the first balloon 2. The sealing may form a circumferential seal 22 around the first balloon 2. The skirt 16 can for example be made of, but is not limited to, a plastic foil or sheet, which may for example be, but is not limited to, glued or welded to the surface 10, and/or may have a size and configuration such that at least upon inflation of the first balloon 2 the distal end 17 of the skirt 16 may be forced tightly against the surface 10.

FIG. 2 shows the first 2 and second balloon 3 in coupled, inflated position, the distal end 8 of the second balloon 3 received inside the pocket 20. The pocket 20 is designed such that upon inflation of the balloons 2, 3 the facing portions 10, 11 of the balloons 2, 3 at least inside the pocket 20 are forced against each other, forming a kissing surface 9. At least part of the second balloon 2 preferably substantially fills the pocket 20. Hence substantially no filling material 208, as will be discussed, can enter into the pocket 20.

In FIG. 1 and FIG. 2, it can be observed that the distal portion 27 of the first balloon 2 can have a first cross section S1, the proximal portion 28 of the first balloon 2 can have a second cross section S2, and the distal end 8 of the second balloon 3 can have a third cross section. In accordance with the exemplary embodiments of the first balloon 2 and the second balloon 3 shown in FIG. 1 and FIG. 2, the third cross section of the distal end 8 of the second balloon 3 can be equal to the cross section S4 of the proximal portion 34 of the second balloon 3. The first cross section S1 of the distal portion 27 of the first balloon 2 can be larger than or equal to a sum of the second cross section S2 of the proximal portion 28 of the first balloon 2 and the third cross section of the distal end 8 of the second balloon 3. The person skilled in the art will appreciate that in this way the flow rate of the blood stream flowing, for example, from the aorta into the iliac vessels can be kept as constant as possible. In addition, disturbances such as, for example turbulences, in the blood stream flowing, for example, from the aorta into the iliac vessels can be reduced in this way.

Figure 2A:
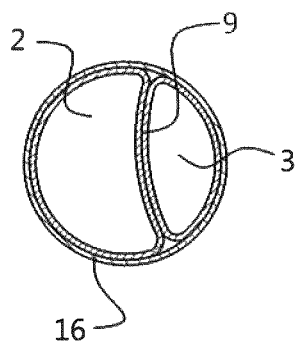
FIG. 2A shows schematically a cross section according to line II-II in FIG. 2.

FIG. 2A schematically shows a cross section of the arrangement of FIG. 2, along the line II-II, across the holding element 7, substantially perpendicular to the longitudinal axis $L_2$ of the first balloon 2. As is shown in FIG. 2A the cross section in general may be substantially circular, defined by the skirt 16, whereas the first and second balloon 2, 3 may both have a flattened, semi-circular cross section within the skirt 16, having surface portions 10, 11 having been forced against each other, forming at least a kissing surface 9. This is made possible by at least the pliability of the balloons 2, 3 and the inflation thereof.

Figure 3A:
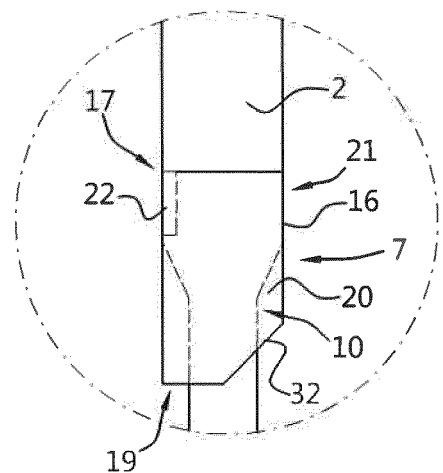
FIG. 3A shows schematically a portion of a first balloon with a holding element, connected to the first balloon at a distal end, inflated by itself.
Figure 3B:
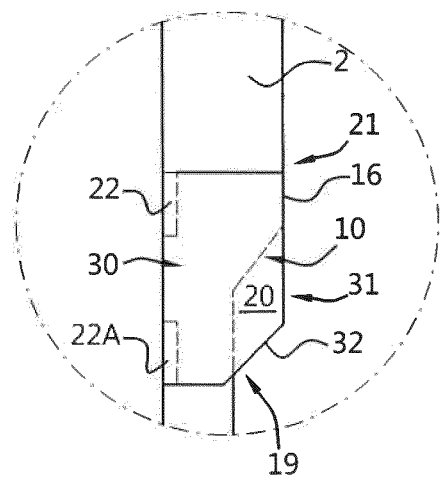
FIG. 3B shows schematically the same portion of a first balloon, with a holding element connected to the first balloon at a distal end and at a proximal end.

FIGS. 3A and 3B show basically two alternatives, by way of example only and without limiting the disclosure, for connection between a skirt 16 and the first balloon 2.

In FIG. 3A the skirt 16 is connected to the surface 10 of the first balloon 2 only at or near the distal end 17, forming a distal connection, which may form a seal 22. The distal connection may extend around part or all of the circumference of the first balloon 2, and may be continuous or comprise one or more individual, spaced apart connections.

In FIG. 3B the skirt 16 is connected to the surface 10 of the first balloon 2 at or near the distal end 17, forming a first, distal connection such as for example a seal 22. The said connection may extend around part or all of the circumference of the first balloon 2, and may be continuous or comprise one or more individual, spaced apart connections. Moreover in FIG. 3B part of a proximal end 19 the skirt 16 is connected to the balloon surface 10, especially a side of the first balloon 2 facing away from the pocket 20, by at least one connection 22A.

As can be seen in e.g. FIGS. 3A and B, the first balloon 2 can be provided with a distal portion 27 and a proximal portion 28, as well as a transition portion 29, connecting the proximal and distal portions 27, 28. When inflated the distal portion can have a cross section $S_1$ at the transition portion 29 which is larger than the cross section $S_2$ of the proximal portion 28 at the transition portion 29, such that the transition portion 29 is widening towards the distal portion 27. The cross sections $S_1$, $S_2$ are considered as being substantially perpendicular to the longitudinal axis $L_2$ of the first balloon 2 and may have any shape but are preferably substantially circular or oval.

In FIG. 3A the transition portion 29 is shown as a portion 29 substantially rotation symmetrical around the longitudinal axis $L_2$ of the first balloon 2, tapering in the proximal direction of the first balloon 2. In this embodiment the pocket 20 may extend all around the first balloon 2. This is also shown in FIGS. 1 and 2, showing that upon insertion into and inflation of the second balloon 3 inside the pocket 20 the transitional section 29 will be pushed mostly to a side, against an inside portion of the skirt 16, the second balloon 3 filling the further pocket 20.

In FIG. 3B an alternative embodiment of especially the transitional portion 29 is shown, in which the transitional portion 29 is not rotational symmetric around the longitudinal axis $L_2$, but is connected to an inside of the skirt 16 at the distal and proximal sides 17, 19 of the skirt 16, such that a first side 30 of the transitional portion 29 is substantially straight and flush with the distal and proximal portions 27, 28, whereas the opposite side 31 is sloping relative to the first side 30 and the longitudinal axis $L_2$. In this embodiment the pocket 20 is mostly at one side of the longitudinal axis $L_2$.

The skirt 16 can in embodiments be substantially cylindrical, at least in a non-deformed state, and in embodiments also in a state when the distal end 8 of the second balloon 3 has been inflated inside the pocket 20, as shown for example in FIGS. 1-3, during use. The holding element 7, especially the skirt 16, can in embodiments be provided at the transition portion 29, preferably extending from the distal portion 27, passing the transitional portion 29 to the proximal portion 28. The distal end 17 of the skirt may be connected to the distal portion 27, whereas the proximal end 19 may surround at least part of the proximal portion 28.

As can be seen in the drawings an edge portion 32 of the proximal end 26 of the skirt 16 at the pocket 20 may be angled relative to the longitudinal axis $L_2$ of the first balloon 2, such that introducing the distal end 8 of the second balloon 3 is easier facilitated. The second balloon 3 may have a distal end 8 which is tapered and/or rounded, such that at least feeding the distal end 8 into the pocket 20 is made easier.

In embodiments the balloons 2, 3 can be substantially straight and cylindrical over their full length between the proximal and distal ends thereof. The distal end 23 and proximal end 24 of the first balloon 2 and the proximal end 25 of the second balloon 3 may be provided with provisions to ensure sealing of the balloons 2, 3 against inside walls of relevant blood vessels 200-204 in which they have to be positioned, such as for example the aorta and iliac veins between which the aneurysm A is provided, if used for bridging an aneurysm in for example the lower aorta or other vessels, such as arteries or veins in a brain area, thoracic area or other parts of the human or animal body. In the embodiments discussed and shown by way of example only, an arrangement of kissing balloons is used for forming a mold to be used for forming a channel bridging an aneurysm in bifurcating blood vessels. It shall however be clear that a similar arrangement can be used for forming other molds, for example for bridging an aneurysm involving more than three vessels.

In embodiments the second balloon 3 can have a proximal end 25 comprising an end portion 33 having, when inflated, a larger cross section $S_3$ than a cross section $S_4$ of a proximal portion 34 of the second balloon 3 directly connected to it. The second balloon 3 can be a half dog bone type balloon.

In embodiments the first balloon 2 can have a proximal end 24 comprising a proximal end portion 35 having, when inflated, a larger cross section $S_5$ than the cross section $S_2$ of a proximal portion 28 of the first balloon 2 directly connected to it. Moreover, a distal end 23 can comprise a distal end portion 36 having, when inflated, a larger cross section $S_6$ than the cross section $S_2$ of a distal portion 27 of the first balloon 2 directly connected to it. The person skilled in the art will appreciate that in this way sufficient filling material can be applied to surround the proximal end portion 35 and the distal end portion 36, respectively. Moreover, said filling material can have a thickness that is sufficient to ensure that the filling material will stay securely in place upon removal of the first balloon 2. In addition, the transition from the larger cross section at for example the distal end portion 36 of the first balloon 2 to the smaller cross section of the distal portion 27 of the first balloon 2 directly connected to it enables a smooth transition between portions of the corresponding part of a lumen of the mold of filling material having a larger cross section and a smaller cross section, respectively. Consequently, the blood flow through said part of the lumen of the mold can smoothly transition from a lower flow rate in the portion of the lumen having the larger cross section to a higher flow rate in the portion of the lumen having the smaller cross section. The first balloon 2 can thus be a half dog bone or a full dog bone type balloon.

Preferably the first balloon 2 is a full dog bone balloon and the second balloon 3 is a half dog bone balloon.

The disclosure discloses an arrangement for effectuating kissing balloons according to an aspect of the invention. A bifurcated vascular structure is shown, such as for example between an aorta and iliac arteries, or a bifurcation of a carotid artery.

In an arrangement 1 the first catheter 5 can comprises a port adapted to supply a suitable fluid for filling the internal lumen 14 of the catheter 5 for expanding the first balloon 2 arranged at or near the distal portion of the catheter 5. The balloon may be a straight balloon having a substantially uniform diameter along its useful length. Alternatively, the balloon may refer to a so-called half or full dog-bone balloon. Similarly, the second catheter 6 can be designed for introducing such fluid into the second balloon 3 for inflating it. In general, and by way of example only without limiting the disclosure, a physiologic salt solution may be used for the suitable filling fluid.

The holding element 7, 16 is preferably firmly attached on a middle portion of the balloon 2 not allowing the holding element 7 to move with respect to its mounting location. For example, the holding element 7 may be suitably glued or welded to the balloon 2.

The arrangement 1, which can comprise the first and second balloons 2, 3 connected to the first and second catheters 5, 6 respectively, can be part of a kit 100. The kit 100 can further comprise a composition 208, which can be referred to as a shapeable material such as a settable composition, which may be a polymeric composition. The kit of parts can further comprise a catheter 101 for introducing the composition 208 into a void, such as an aneurysmal sac A. The catheter 101 can be a separate catheter or can be an integral part of the first or second catheter 5, 6, for example by providing the relevant catheter as a multi lumen catheter, one of the lumen having an outlet opening into the sac when the balloons are properly positioned inside such sac A.

It will be appreciated that the composition 208, which may also be referred to as for example a settable composition, such as a settable polymer composition and/or a shapeable material may be introduced in vivo or ex-vivo (for training purposes, for example) around the arrangement 1 having durable kissing surfaces 10, 11; 9 between the expanded balloons 2, 3. When the composition 208 assumes its final shape and form the catheters 5, 6 may be extracted leaving a bifurcated lumen 210 within the composition 208.

The composition 208 may in principle be any biocompatible composition. In particular suitable are polymer compositions comprising a physiologically acceptable (pre)polymer, such as polyurethane (pre)polymer or a silicone (pre) polymer.

Such compositions are known in the art per se. Suitable polyurethane (pre)polymer compositions are e.g. known from U.S. Pat. No. 7,670,622 or 6,306,177, which are incorporated herewith by reference as particular embodiment of the invention. Suitable silicone (pre)polymer compositions are e.g. known from EP-A 1 435 249 which is incorporated herewith by reference as a suitable embodiment of the invention. Further examples of compositions include biopolymer compositions, e.g. as described in WO 95/08289 and epoxy resins, e.g. as described in EP 0 667 131 A2, which are incorporated herewith by reference. Particularly suitable is a composition as described in WO 2017/086791 or in WO 2017/086793, which are incorporated by reference.

Such compositions can be introduced in vivo in a fluid state and cured in vivo, to form an essentially solid structure.

Preferably, the composition meets at least one, at least two or at least three of the following conditions:
  the (uncured) composition has a viscosity of 2 000 to 12 000 cSt at 25° C.
  the composition is curable in the presence of a curing catalyst at 37° C. to form a cured material with an elongation until rupture of at least 5%, preferably of 25-500%, in particular of 50-250%
  the composition is curable in the presence of a curing catalyst at 37° C. to form a cured material with an elastic modulus of at least 1 MPa, in particular 2-40 MPa, more in particular 3-20 MPa after curing of the composition, the resulting material has a stress value of at least 5 kPa at 1% strain, more preferably of at least 30 kPa at 20% strain, even more preferably a stress value of at least 1 MPa at 50% strain The viscosity as defined herein is the kinematic viscosity in cSt as measured by Brookfield viscosimeter (UK), model ND J-1 and/or rheometer RMS 800 from Rheometrics, USA. The kinematic viscosity of a fluid in cSt corresponds to the dynamic viscosity in mPa·s divided by the density of the fluid in g/cm$^3$.

Additionally or alternatively, the composition preferably meets the following condition: the (uncured) composition has a viscosity of 2 000 to 12 000 cSt at 25° C. wherein the viscosity is the kinematic viscosity in cSt as determined from the dynamic viscosity in mPa·s measured by Rheometer Haake Mars iQ-Air with Peltier temperature module and 35 mm cone/1 degree angle from Thermo Fisher Scientific USA. The kinematic viscosity of a fluid in cSt corresponds to the dynamic viscosity in mPa·s divided by the density of the fluid in g/cm$^3$.

The elongation until rupture as defined herein is the value as measured by a Zwick 1445 tensile strength tester (Germany).

The elastic modulus as defined herein is the value as measured by dynamic mechanical analyser, DMA 7 from Perkin-Elmer (USA).

The stress value as defined herein is the value as determined with Zwick 1445 or with DMA 7, Perkin-Elmer).

Suitable compositions having a viscosity of 2 000 to 12 000 cSt and/or being curable to form a cured material with an elongation until rupture of at least 5%, preferably at least 25%, and an elastic modulus of at least 1 MPa, are known from EP-A 1 435 249. The content of the publication is incorporated by reference, in particular with respect to details on the content of the composition and manners to administer the polymer composition to a body vessel and cure the composition.

Preferably the composition comprises a polydialkylsiloxane (pre-) polymer, in particular a polydimethylsiloxane homo- or copolymer, having at least two vinyl groups, as described in EP-A 1 435 249. The contents hereof with respect to the polydialkylsiloxane (pre-) polymer, in particular paragraphs [0046]-[0048], are incorporated by reference.

In a particularly suitable embodiment, the composition further comprises a filler and a curing agent. In particular, the filler and/or curing agent may be selected from those disclosed in EP-A 1 435 249. The contents hereof with respect to the filler and the curing agent, in particular paragraphs [0051]-[0067] are incorporated by reference.

The composition may comprise one or more (further) additives, in particular one or more additives selected from the group of contrast agents, curing inhibitors and chain extenders, e.g. as described in EP-A 1 435 249, paragraphs [0069]-[0071], which paragraphs are incorporated herein by reference.

Further, a curing catalyst may be included. If the composition is provided in a kit, the curing catalyst is preferably included in a separate container in the kit. The catalyst is then mixed with the composition briefly before administering the composition in vivo. The catalyst preferably is a platinum complex, e.g. as described in EP-A 1 435 249, paragraphs [0075]-[0078], which paragraphs are incorporated by reference.

At least one of the first and second catheter 5, 6, the first and second balloon 2, 3 and the holding element 7 may comprise at least one marker, especially a radiopaque marker, preferably at least two such markers 40. Use of the markers 40 may make proper positioning of the relevant parts of the kit 100 easier.

The disclosure is further related to a method of manufacturing an arrangement for implementing kissing balloons 2, 3 for simulating a bifurcation. The method comprises the steps of providing the first catheter 5 having the first inflatable balloon 2 with the holding element 7 arranged on the said first balloon 2, and an inflatable second balloon 3 provided on the second catheter 6. The holding element 7, 16 is, as discussed, adapted for receiving and holding the distal end 8 of the second inflatable balloon 3, such that, in use, respective facing surfaces 10, 11 of the first inflated balloon 2 and the second inflated balloon 3 are pressed against each other within the holding element 7, forming the kissing surface 9 within the holding element 7.

Figure 4:
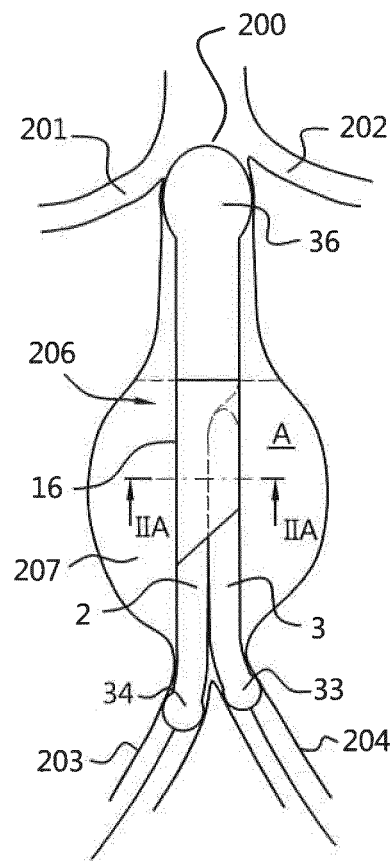
FIG. 4 shows in a schematic way an embodiment of forming a mold for forming a channel bridging an aneurism at a vascular bifurcation using an arrangement according to an aspect of the invention.

In an embodiment in a method according to the disclosure, which is here discussed by way of example only, without limiting the disclosure, for treatment of an aneurysm A in a lower part of an aorta 200, between the renal arteries 201, 202 and the iliac arteries 203, 204 as shown in FIG. 4. The aorta may also be referred to as a communal artery or a main vessel 200, the iliac arteries may also be referred to as first and second vessel 203, 204.

The first balloon 2 is introduced into a first blood vessel, for example a first iliac artery 203 in a first leg of a patient, in a collapsed state in a known manner, for example using a guide wire $G_2$, which may for example extend through the balloon 2 or through the holding element, for example through an opening in the skirt 16. The first balloon 2 is fed through said first vessel 203 up into and partly through the aneurysm A in the first vessel, such as the aorta 200, such that the distal end portion 36 is introduced into the aorta 200 above the aneurysm, i.e. at a cranial side thereof, below the renal arteries 201, 202, in healthy portion thereof. The proximal end portion 35 is positioned inside the relevant first vessel, such as the iliac artery 203, again in a healthy portion thereof.

The second balloon 3 is introduced into a second blood vessel, for example a second iliac artery 204 in a second leg of a patient, in a collapsed state in a known manner, for example using a guide wire $G_3$, which may for example be fed into or through the holding element, after properly positioning the first balloon 2. The second balloon 3 is fed through said second vessel 204 up into the aneurysm A, such that the distal end 8 is introduced into the sack 20 in de holding element, shown as a skirt 16 as discussed. The distal end 8 is preferably fed all the way up into the pocket 20. The proximal end portion 33 is positioned in the end of the second vessel 204, such as the second iliac artery 204, again in a healthy portion thereof.

The first and second balloons 2, 3 are inflated, simultaneously or sequentially, such that the distal end portion 36 is pressed against an inside wall of the main vessel, the aorta 200, substantially and preferably completely closing off said main vessel 200, whereas the proximal end portion 35 is pressed against the inside wall of the first vessel such as the first iliac vessel 203, closing it substantially off and preferably completely. Moreover, the proximal end portion 33 of the second balloon 3 is pressed against the inside wall of the second vessel such as the second iliac vessel 203, closing it substantially off and preferably completely too. Thus, the first and second balloon 2, 3 are fixed in position temporarily.

Figure 5:
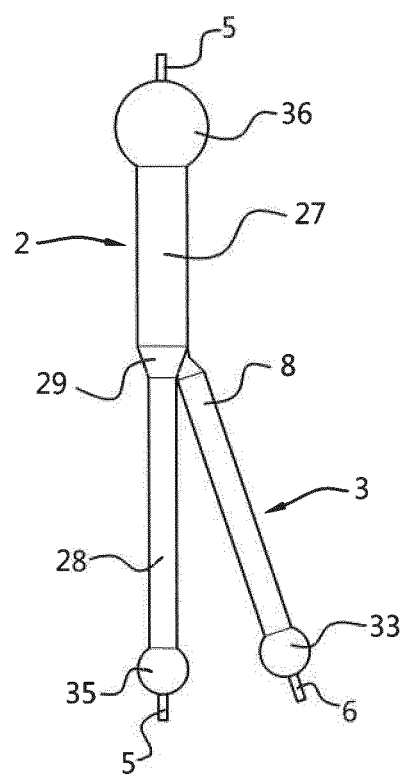
FIG. 5 shows a schematic view of two balloons according to the present disclosure, without a holding element.

As can be seen in FIG. 5 by way of example, in which the holding element is not shown, the distal and proximal ends 35, 36 of the first balloon 2 and the proximal end 33 of the second balloon 3 can be substantially spherical.

Upon inflating the balloons 2, 3 the distal end 8 is also enclosed inside the pocket 20, such that the distal portion of the second balloon 3 substantially fills the pocket 20, as for example shown in FIGS. 2 and 2A, 4 and 6.

Figure 6:
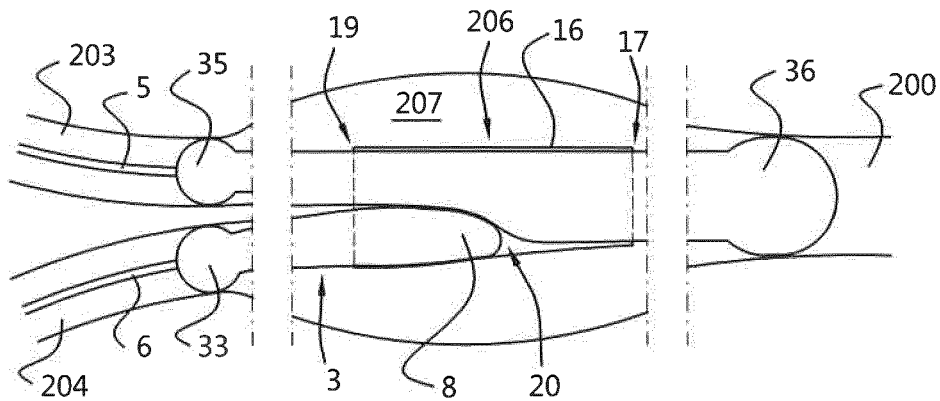
FIG. 6 shows schematically part of an arrangement of the disclosure, showing a distal end of a second balloon inserted into a pocket at the first balloon, showing a kissing surface between the first and second balloon.

In this position, as schematically shown in FIGS. 4 and 6, a mold 206 is formed, bridging the aneurysm A, which defines an aneurysmal sac portion 207 isolated from the actual blood vessels 200-204.

Figure 7:
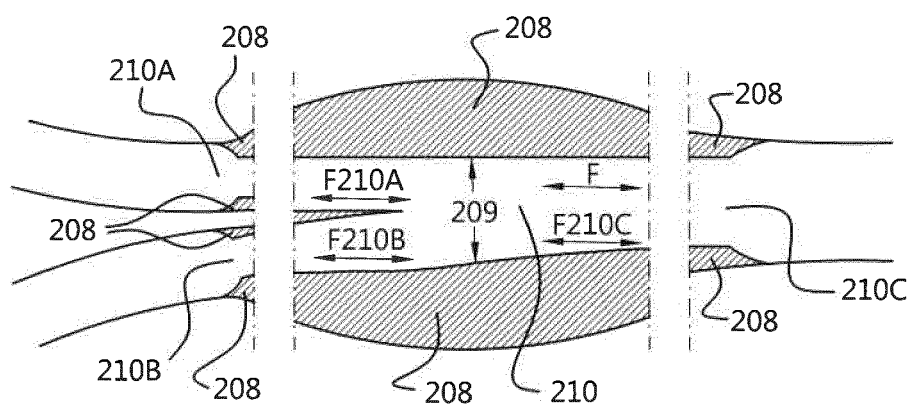
FIG. 7 shows schematically an aneurysm with a channel bridging the aneurysm, formed by a settable material, using an arrangement of the disclosure.
Figure 8:
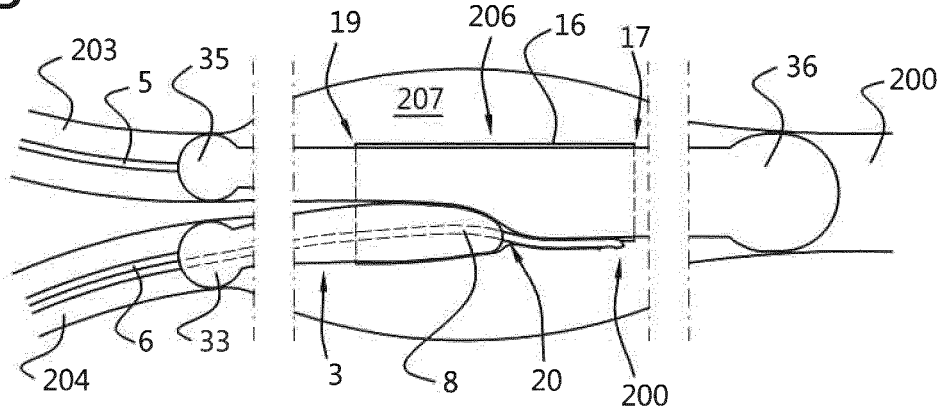
FIG. 8 shows an arrangement according to FIG. 6, with a second catheter having dual lumen.

After forming such mold 206 the composition 208 may be introduced into the sac portion 207. To this end a separate catheter can be used or a lumen 6A of the for example second catheter having a distal opening 200 which opens into the sac portion 207 near the distal end of the second balloon 3 preferably outside the skirt 16 is prevented from flowing further into the vessels 200-204 by the distal end portion 36 of the first balloon 2 and the proximal end portions 35, 33 of the first and second balloons 2, 3, as is shown especially in FIGS. 6 and 7. The composition 208 is allowed to set, such that it becomes substantially form stable, and having a surface 209 at least facing, especially contacting the mold 206, which surface 209 is substantially continuous, preferably substantially free of crevices, dead volumes or the like, and which surface 209 is preferably closed and impermeable to blood. The composition 208 may be settable in any suitable way, for example by chemical or mechanical reactions and may for example be initiated or catalyzed by light introduced into the composition in a known manner, for example through a catheter.

After setting of the composition 208 the catheters 5 and 6 may be removed, by deflating the balloons 2, 3 and retracting them through the vessel 203, 204 respectively. This leaves a bifurcated channel 210, defined by the composition 208 set. The bifurcated channel 210 bridges the aneurysm A. Flow through the channel 210 is not hindered by irregularities in the surface 209, such as dead spaces in which blood could be received and in which for example clogging could occur.

The flow pattern through the channel 210 is optimized by the systems and methods according to the disclosure, relative to the prior art as discussed. As can be seen in the drawings the bifurcating channel parts 210A, 210B leading into the first and second vessels, such as the iliac arteries 203, 204 have, where they connect into the single channel part 210C leading into the main vessel 200, such as the aorta 200, have a main flow direction $F_{210A}$, $F_{210B}$ substantially parallel to each other, and to the main flow direction $F_{210C}$. It should be noted that the flow F through the bifurcated vessel can be either direction, i.e. from the main vessel 200 to the first and second vessels 203, 204 or in opposite direction. The substantially parallel, i.e. laminar, flow directions $F_{210A, B, C}$ can improve the flow pattern, for example by limiting turbulence in the channel 210.

In order to enable visualization of the first and/or second catheter 5, 6, the first and/or second balloon 2, 3 and/or the holding element 7, with respect to the patient's anatomy, at least one of these may be provided with a suitable radiopaque structure 40. By way of example, in some embodiments radiopaque material may be provided on a proximal and/or distal end of the holding element 7, such as the skirt 16 and/or at least the second balloon 3 and/or the second catheter 6 near the distal and 13 thereof.

While specific embodiments have been described above, it will be appreciated that the invention may be practiced otherwise than as described. Moreover, specific items discussed with reference to any of the figures may freely be inter-changed supplementing each other in any particular way. The descriptions above are intended to be illustrative, not limiting. Thus, it will be apparent to one skilled in the art that modifications may be made to the invention as described in the foregoing without departing from the scope of the claims set out below.

The invention claimed is:

1. An arrangement for implementing kissing balloons simulating a bifurcated vessel, comprising:
a first catheter having a first inflatable balloon, a second catheter having a second inflatable balloon, wherein the first balloon comprises a holding element that is adapted to receive and hold a distal end of the second balloon inside the holding element and upon inflation of the first balloon and the second balloon to allow formation of a kissing surface between respective facing surfaces of the first balloon and the second balloon inside the holding element, wherein the holding element is designed and connected to the first balloon to prevent the distal end of the second balloon from extending beyond a distal end of the holding element.

2. The arrangement according to claim 1, wherein the holding element at least comprises or is formed by a skirt extending around at least part of the first balloon, providing for a pocket into which the distal end of the second balloon is insertable.

3. The arrangement according to claim 2, wherein the skirt is connected to the first balloon, sealing the skirt against the first balloon.

4. The arrangement according to claim 3, wherein the first balloon is provided with a distal portion and a proximal portion, as well as a transitional portion connecting the proximal portion and the distal portion, wherein when the first balloon is inflated the distal portion has a cross section (S1) at the transitional portion which is larger than a cross section (S2) of the proximal portion at the transitional portion, such that said transitional portion is widening towards the distal portion, and wherein the holding element is provided at the transitional portion, extending from the distal portion, across the transitional portion to the proximal portion.

5. The arrangement according to claim 4, wherein the second balloon distal end is tapered and/or rounded, and wherein at least the second balloon is provided at a distal end of the second catheter, and wherein the first balloon is provided at a distal end of the first catheter.

6. The arrangement according to claim 5, wherein the second balloon has a proximal end comprising an end portion that, when the second balloon is inflated, has a larger cross section than a portion of the proximal end of the second balloon that is directly connected to said end portion, wherein the second balloon is a half dog bone type of balloon, and wherein the first balloon has a proximal end comprising a proximal end portion that, when the first balloon is inflated, has a larger cross section than a proximal portion of the proximal end of the first balloon that is directly connected to said proximal end portion, and a distal end comprising a distal end portion that, when the first balloon is inflated, has a larger cross section than a distal portion of the distal end of the first balloon that is directly connected to said distal end portion, wherein the first balloon is a full dog bone type of balloon.

7. The arrangement according to claim 6, wherein the distal end of the second balloon has a third cross section (S4), and wherein the first cross section (S1) is larger than or equal to a sum of the second cross section (S2) and the third cross section (S4).

8. A kit of parts, comprising: the arrangement according to claim 7 and a settable composition, preferably a polymeric composition, wherein the kit of parts further comprises a catheter for introducing the settable composition into a void, such as an aneurysmal sac.

9. The kit of parts according to claim 8, wherein at least one of the first catheter and the second catheter, the first balloon and the second balloon and the holding element comprises at least one marker.

10. The arrangement according to claim 3, wherein sealing the skirt against the first balloon comprises forming a circumferential seal around the first balloon.

11. The arrangement according to claim 1, wherein the first balloon is provided with a distal portion and a proximal portion, as well as a transitional portion connecting the proximal portion and the distal portion, wherein when the first balloon is inflated the distal portion has a cross section (S1) at the transitional portion which is larger than a cross section (S2) of the proximal portion at the transitional portion, such that said transitional portion is widening towards the distal portion.

12. The arrangement according to claim 11, wherein the holding element is provided at the transitional portion, extending from the distal portion, across the transitional portion to the proximal portion.

13. The arrangement according to claim 11, wherein the distal end of the second balloon has a third cross section (S4), and wherein the first cross section (S1) is larger than or equal to a sum of the second cross section (S2) and the third cross section (S4).

14. The arrangement according to claim 1, wherein the second balloon distal end is tapered and/or rounded.

15. The arrangement according to claim 1, wherein at least the second balloon is provided at a distal end of the second catheter, and wherein the first balloon is provided at a distal end of the first catheter.

16. The arrangement according to claim 1, wherein the second balloon has a proximal end comprising an end portion that, when the second balloon is inflated, has a larger cross section than a portion of the proximal end of the second balloon that is directly connected to said end portion, wherein the second balloon is a half dog bone type of balloon.

17. The arrangement according to claim 1, wherein the first balloon has a proximal end comprising a proximal end portion that, when the first balloon is inflated, has a larger cross section than a proximal portion of the proximal end of the first balloon that is directly connected to said proximal end portion, and a distal end comprising a distal end portion that, when the first balloon is inflated, has a larger cross section than a distal portion of the distal end of the first balloon that is directly connected to said distal end portion, wherein the first balloon is a full dog bone type of balloon.

18. A kit of parts, comprising: the arrangement according to claim 1 and a settable composition, preferably a polymeric composition, wherein the kit of parts further comprises a catheter for introducing the settable composition into a void, such as an aneurysmal sac.

19. The kit of parts, according to claim 18, wherein at least one of the first catheter and the second catheter, the first balloon and the second balloon and the holding element comprises at least one marker.

20. The kit of parts according to claim 19, wherein the at least one marker comprises a radiopaque marker.

21. The kit of parts according to claim 19, wherein the at least one marker comprises at least two markers.

22. A method of manufacturing an arrangement for implementing kissing balloons for simulating a bifurcated vessel, the method comprising the steps of:
providing a first catheter having a first inflatable balloon with a holding element arranged on said first balloon, and
providing a second catheter having a second inflatable balloon, wherein said holding element is adapted to receive and hold a distal end of the second inflatable balloon inside the holding element upon inserting the distal end of the second balloon in the holding element, wherein upon inflating the first balloon and the second balloon, in use of the arrangement, a kissing surface is formed between respective facing surfaces of the first balloon and the second balloon inside the holding element, wherein the holding element is designed and connected to the first balloon to prevent the distal end of the second balloon from extending beyond a distal end of the holding element.

* * * * *